United States Patent [19]

Repenning

[11] Patent Number: 5,314,475
[45] Date of Patent: May 24, 1994

[54] METHOD FOR PRODUCING OSTEO-INTEGRATING SURFACES ON SKELETAL IMPLANTS AND SKELETAL IMPLANTS WITH OSTEO-INTEGRATING SURFACES

[76] Inventor: Detlev Repenning, Krabbenhöhe 12,, 2057 Reinbek, Fed. Rep. of Germany

[21] Appl. No.: 48,579

[22] Filed: Apr. 16, 1993

Related U.S. Application Data

[63] Continuation of Ser. No. 656,301, Feb. 15, 1991, abandoned.

[30] Foreign Application Priority Data

Mar. 23, 1990 [DE] Fed. Rep. of Germany ....... 4009337

[51] Int. Cl.⁵ .................... A61F 2/28; A61F 2/30; A61F 2/54; A01N 1/02
[52] U.S. Cl. ............................. 623/16; 623/18; 623/901; 623/66; 427/2
[58] Field of Search .............. 623/16, 18, 901, 66; 427/2

[56] References Cited

U.S. PATENT DOCUMENTS 4,965,088 10/1990 Shimamune et al. ................ 623/16

FOREIGN PATENT DOCUMENTS 0248117 12/1987 European Pat. Off. .............. 623/18
2595572 9/1987 France .................................. 623/18
2286158 11/1990 Japan .................................... 623/18

OTHER PUBLICATIONS

Ullman's Encyclopedia of Industrial Chemistry, 5th Edition, VCH Publisher's, 1989, vol. A20, pp. 427-437.
Ullman's Encyclopedia of Industrial Chemistry, 5th revised edition, VCH Publisher's, 1989, vol. A6, pp. 69-74.
Ullman's Encyclopedia of Industrial Chemistry, 5th revised edition VCH Publisher's, 1989, vol. A16, pp. 429-438.

*Primary Examiner*—Randall L. Green
*Assistant Examiner*—Dinh X. Nguyen
*Attorney, Agent, or Firm*—Robert W. Becker & Associates

[57] ABSTRACT

A method for producing osteo-integrating surfaces of skeletal implants that are made from metal or metal alloys and skeletal implants having osteo-integrating surfaces are provided. The method consists of the steps of coating the skeletal implant with an oxide layer by a high vacuum plasma coating process and subsequently applying a calcium hydroxyl apatite layer onto the oxide layer.

10 Claims, 1 Drawing Sheet

Fig. 1
Fig. 2
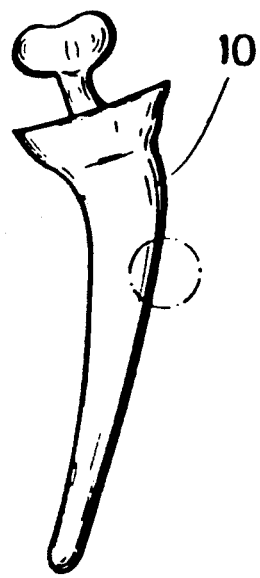
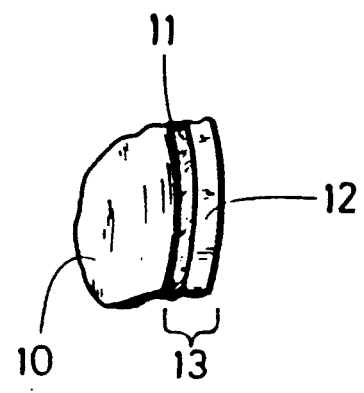

METHOD FOR PRODUCING OSTEO-INTEGRATING SURFACES ON SKELETAL IMPLANTS AND SKELETAL IMPLANTS WITH OSTEO-INTEGRATING SURFACES

This application is a continuation, division, of application Ser. No. 656,301 filed Feb. 15, 1991, now abandoned.

BACKGROUND OF THE INVENTION

The present invention relates to a method for producing osteo-integrating surfaces on skeletal implants (substrates) that are made from metal or metal alloys and to skeletal implants having an osteo-integrating surface.

Skeletal implants require a high strength and resistance but also a good compatibility with the surrounding biological medium or tissue. Metals or metal alloys have been employed as skeletal implant materials for some time. Such skeletal implants, upon insertion into the biological medium, respectively tissue, are known to form a surface oxide layer in that specific medium at random. In the past, skeletal implants made from titanium have been implanted without applying any outer coating, whereby, due to a reaction in the biological medium, a titanium dioxide layer is formed more or less randomly, on the surface of the titanium material. It has also been tried to form a titanium dioxide coating or layer on the titanium skeletal implants by an anodic coating process before the implants are introduced into the biological medium. The titanium dioxide layers resulting from this process usually have a thickness of $4 \times 10^{-7}$ m.

However, the randomly formed coatings have proven to be too thin, are porous and easily damaged. The coatings or layers applied by the anodic coating process usually have the same drawbacks. Once an oxide layer has been damaged, the damaged areas lead to friction-induced corrosion and also to the formation of titanium compounds of a low oxidation state. These titanium compounds in general cause necrosis in the surrounding body tissue.

Another problem of the known skeletal implants is that the skeletal implant in general does not bond in the desired manner to the bone it is implanted in. It has been tried to overcome this problem by providing the skeletal implant with a porous surface in order to increase the surface area available for adhesion respectively ingrowth, of the surrounding tissue. However, this measure is not successful in all cases. Also, the adhesion of the implant to the bone lacks sufficient strength. It is therefore an object of the present invention to provide a method for applying oxide layers or coatings onto skeletal implants, whereby these oxide layers, on the one hand, provide excellent integration characteristics into the biological medium, are uniformly applicable and also have a high mechanical resistance, and, on the other hand, also provide good osteo-integrating characteristics. The method should also be easy to perform. A skeletal implant that has excellent integration characteristics into the biological medium, is uniformly applicable and also has a high mechanical resistance, while, at the same time, demonstrates good osteo-integrating characteristics, is provided as well.

BRIEF DESCRIPTION OF THE DRAWINGS

This object, and other objects and advantages of the present invention, will appear more clearly from the following specification in conjunction with the accompanying drawings, in which:

FIG. 1 is a side view of a skeletal implant for the implantation into a human femur; and FIG. 2 shows a section of the surface of the skeletal implant represented in FIG. 1.

SUMMARY OF THE INVENTION

The method for producing osteo-integrating surfaces of skeletal implants (substrates) of the present invention is primarily characterized by coating the skeletal implant with an oxide layer by a high vacuum plasma coating process and subsequently applying a calcium hydroxyl apatite layer onto the oxide layer.

The advantage of the present invention is that, due to the high metal content of the plasma and the high ion energy of the evaporating metals that contain oxygen in a bonded or nonbonded form, surfaces of a high adhesion and a high density are created. The surfaces are also free of pores so that the disadvantageous corrosion effects known from the skeletal implants of the prior art are prevented. Calcium hydroxyl apatite which is used to form the second outer layer of the skeletal implant is a natural constituent of the skeleton and the teeth of humans and mammals. Accordingly, bone tissue easily grows into calcium hydroxyl apatite structures. Since calcium hydroxyl apatite, even when applied as a coating, is of a micro-porous structure the bone tissue also grows into the lower oxide layer, i.e., it grows through the calcium hydroxyl apatite layer into the oxide layer. Thus, osteo-integrating surfaces are formed on the substrate.

The electric arc evaporation technique is advantageously employed as a coating process for the application of the oxide layer. In this technique, the plasma has a high metal content. Equally advantageous are coating processes according to the laser evaporation method or the so-called wire-explosion method, both of which are also characterized by a plasma having a high metal content.

Preferably, the oxides for the manufacture of the oxide layers or coatings are selected from refractory metal oxides. Preferred refractory metals are titanium, zirconium, hafnium, niobium, tantalum, tungsten or molybdenum. According to a further advantageous embodiment, the oxide layers or coatings comprise a system of a plurality of refractory metal oxides. For example, a system consisting of titanium/zirconium oxide may be used to form the oxide layer. Advantageously, a system consisting of titanium/niobium oxide may also be employed.

According to a further preferred embodiment, the calcium hydroxyl apatite layer is applied onto the oxide layer by spray coating.

It may also be advantageous to apply the calcium hydroxyl layer onto the oxide layer by annealing.

Independent of the manner chosen for applying the calcium hydroxyl apatite layer onto the first oxide layer, the oxide layer is selected such that a chemical bonding is achieved between the calcium hydroxyl apatite and the oxide, and that good in-growth characteristics of the biological medium are ensured. Also, the oxide has a good compatibility with the biological medium.

The skeletal implant made from a metal or metal alloy and having an osteo-integrating surface is characterized by having a coating that comprises at least two layers, whereby a first one of the layers is an oxide layer that is disposed directly on the skeletal implant, and a second one of the layers is a calcium hydroxyl apatite layer that is disposed as an external layer.

The skeletal implant of the present invention has the advantage of providing excellent integration characteristics in the biological medium and of providing an osteo-integrating surface on the skeletal implant which forms a connection between the bone and the implant that is mechanically solid and strong. The first layer which is an oxide layer is preferably formed from refractory metal oxides such as the oxides of titanium, zirconium, hafnium, niobium, tantalum, tungsten and molybdenum.

DESCRIPTION OF PREFERRED EMBODIMENTS

The present invention will now be described in detail with the aid of a specific embodiment utilizing FIGS. 1 and 2.

The skeletal implant 10 may, for example, consist of titanium or titanium alloys, cobalt-bromine-molybdenum alloys or any other metal or metal compounds or metal alloys. According to the method of the present invention, a first layer 11 consisting of an oxide of the refractory metals is applied, for example, by a high vacuum plasma coating process. Onto this first layer 11, a second layer 12 is applied, which consists of calcium hydroxyl apatite $Ca_5[(OH)(PO_4)]_3$. Apatite of this formula is also a constituent of the skeleton (bones, teeth) of humans and mammals.

The first layer 11 consisting of a refractory metal oxide and the second layer 12 consisting of calcium hydroxyl apatite together form the outer coating 13 of the skeletal implant 10. The first layer 11, however, may comprise a multi-component metal oxide system. Such multi-component metal oxide systems are, for example, titanium/zirconium oxide or titanium/niobium oxide. In other words, the first layer 11 may comprise a plurality of different suitable layers or layer systems.

Calcium hydroxyl apatite which is forming the second outer layer 12 is micro-porous, so that bone tissue into which the skeletal implant 10 of the present invention is inserted may easily grow in. The bone tissue may also grow into the underlying oxide layer 11 due to the micro-porous structure of the second layer 12.

An advantage of the method of the present invention and of the skeletal implant that is produced according to the present invention is that with so-called encapsulating metals from which the skeletal implant is made, for example, a cast of Co-Cr-Mo (cobalt-chromium-molybdenum) alloy, the non-porous surface thereof is sealed chemically against the surrounding tissue so that a high biological compatibility is achieved.

The present invention is, of course, in no way restricted to the specific disclosure of the specification, examples and drawings, but also encompasses any modifications within the scope of the appended claims.

What I claim is:

1. A method for producing osteo-integrating surfaces on skeletal implants, said skeletal implants being made from metal or metal alloys, said method comprising the steps of:

coating said skeletal implant with a layer of an oxide by a high vacuum plasma coating process, wherein in said high vacuum plasma coating process a plasma consisting of said oxide is generated and said plasma consisting of said oxide is deposited on said skeletal implant to form said layer of said oxide; and subsequently applying a calcium hydroxyl apatite layer onto said layer of said oxide.

2. A method according to claim 1, in which said oxides are oxides of refractory metals.

3. A method according to claim 2, in which said refractory metals are selected from a group consisting of titanium, zirconium, hafnium, niobium, tantalum, tungsten and molybdenum.

4. A method according to claim 1, which includes the step of spray-coating said calcium hydroxyl apatite layer onto said oxide layer.

5. A method according to claim 1, which includes the step of annealing said calcium hydroxyl apatite layer onto said oxide layer.

6. A skeletal implant made from metal or metal alloy and having an osteo-integrating surface prepared by a process comprising the steps of;

coating said skeletal implant with a layer of an oxide by a high vacuum plasma coating process, wherein in said high vacuum plasma coating process a plasma consisting of said oxide is generated and said plasma consisting of said oxide is deposited on said skeletal implant to form said layer of said oxide; and subsequently applying a calcium hydroxyl apatite layer onto said layer of said oxide.

7. A skeletal implant according to claim 6, wherein said oxide layer is made from oxides of refractory metals.

8. A skeletal implant according to claim 6, wherein said refractory metals are selected from a group consisting of titanium, zirconium, hafnium, niobium, tantalum, tungsten and molybdenum.

9. A method for producing osteo-integrating surfaces on skeletal implants, said skeletal implants being made from metal or metal alloys, said method comprising the steps of;

coating said skeletal implant with a layer of an oxide by a high vacuum plasma coating process, said high vacuum plasma coating process comprising the steps of;
   a) generating a plasma consisting of said oxide;
   b) depositing said plasma consisting of said oxide on said skeletal implant to form said layer of said oxide; and subsequently applying a calcium hydroxyl apatite layer onto said layer of said oxide.

10. A skeletal implant made from metal or metal alloy and having an osteo-integrating surface prepared by a process comprising the steps of;

coating said skeletal implant with a layer of an oxide by a high vacuum plasma coating process, said high vacuum plasma coating process comprising the steps of;
    a) generating a plasma consisting of said oxide;
    b) depositing said plasma consisting of said oxide on said skeletal implant to form said layer of said oxide; and subsequently applying a calcium hydroxyl apatite layer onto said layer of said oxide.

* * * * *